(12) United States Patent
Eidsen et al.

(10) Patent No.: US 7,294,120 B1
(45) Date of Patent: Nov. 13, 2007

(54) AUTOMATED INSTILLATION APPARATUS AND METHOD

(75) Inventors: Jeff Brian Eidsen, Windsor, CA (US); Cindy Carol Eidsen, Windsor, CA (US); Bruno Mombrinie, Santa Rosa, CA (US); Joe Peterson, Windsor, CA (US); Robert Davis, Santa Rosa, CA (US)

(73) Assignee: Haleys Pump Company, Forestville, CA (US)

( * ) Notice: Subject to any disclaimer, the term of this patent is extended or adjusted under 35 U.S.C. 154(b) by 709 days.

(21) Appl. No.: 10/419,325

(22) Filed: Apr. 18, 2003

Related U.S. Application Data

(60) Provisional application No. 60/373,797, filed on Apr. 18, 2002.

(51) Int. Cl.
*A61M 5/00* (2006.01)
(52) U.S. Cl. .................................... 604/257
(58) Field of Classification Search ............... 604/257, 604/259, 246, 183–186
See application file for complete search history.

(56) References Cited

U.S. PATENT DOCUMENTS

| | | | |
|---|---|---|---|
| 3,929,157 A * | 12/1975 | Serur | 137/453 |
| 5,807,333 A * | 9/1998 | Osborne et al. | 604/131 |
| 6,106,506 A * | 8/2000 | Abell et al. | 604/275 |
| 6,460,543 B1 * | 10/2002 | Forsell | 128/898 |
| 6,595,971 B1 * | 7/2003 | von Dyck et al. | 604/334 |
| 6,695,825 B2 * | 2/2004 | Castles | 604/332 |
| 6,752,790 B2 * | 6/2004 | Coombs | 604/251 |
| 6,840,923 B1 * | 1/2005 | Lapcevic | 604/319 |

* cited by examiner

*Primary Examiner*—Nicholas D. Lucchesi
*Assistant Examiner*—Melissa A McCorkle
(74) *Attorney, Agent, or Firm*—Gary Hoenig

(57) ABSTRACT

An automated instillation apparatus and method for instilling fluid into a patient having an intestinal stoma thereby administering an antegrade colonic enema. The automated instillation apparatus comprising in combination: a fluid reservoir, a pump, a pump control module, a fluid delivery line and an intestinal stoma catheter wherein the pump control module is operable to automatically stop fluid delivery to the intestinal stoma after a predetermined volume of fluid has been instilled at a predetermined flow rate and pressure range suitable for the particular patient. The automated instillation apparatus is optionally battery powered and of a size and weight suitable for carrying on a person. The automated instillation apparatus enables a method for a patient to self-administer an antegrade colonic enema within a short time period and with improved privacy by filling a fluid reservoir, inserting an intestinal stoma catheter into the patient with such a stoma opening and activating the apparatus to transfer fluid to the intestine without further intervention.

11 Claims, 4 Drawing Sheets

AUTOMATED INSTILLATION APPARATUS AND METHOD

This application is a Continuation-In-Part of U.S. Provisional Patent Application Ser. No. 60/373,797 filed Apr. 18, 2002, for which priority is claimed and whose disclosure is hereby incorporated by reference in its entirety.

The present invention relates to a human large intestine flushing apparatus such as required for patients with large intestinal disorders including fecal incontinency or intractable constipation. More particularly, to an apparatus for automatic instillation of flushing fluids to the large intestine for managing bowel movements in patients exhibiting fecal incontinency, intractable constipation or related disorders who have undergone a Malone type, Monti plasty or similar surgical procedure wherein a catheterizable stoma is constructed into the large intestine allowing insertion of the instillation apparatus for the purpose of administering an Antegrade Colonic or Continent Enema (ACE).

BACKGROUND OF THE INVENTION

Medical disorders of the large intestine can result in symptoms which prevent the patient from adequately evacuating fecal material from the large intestine. Fecally incontinent and intractably constipated patients have difficulties managing their bowel movement. Bowel movement management is typically accomplished by a daily flushing of the large intestine by enema wherein fluids are introduced into the large intestine to flush materials retained in the intestine. Fluids can be introduced from the rectum and allowed to drain out. There are disadvantages with the application of a rectal enema flush including the lack of penetration of fluid into the large intestine, thereby leaving fecal matter lodged in the intestine, cleanliness issues, general difficulty of self application, lack of privacy, discomfort, and bulky enema equipment.

Surgical techniques have been developed to permit the application of an enema into the large intestine from the top of the intestine as opposed to the rectum. The enema from above or Antegrade Colonic Enema requires that a patient undergo a surgical procedure to create a stoma or entry through the skin into the intestine proximal to the top of the large intestine, principally to the cecum. Fluids are introduced and permitted to flush and drain to and out the rectum. Several surgical procedures have been developed to construct an entry point intestinal stoma proximal to the cecum. The Malone or Continent Appendicostomy surgical procedure constructs a connection conduit made between the appendix and the navel (belly-button) wherein a "button" or piercing is created at the navel. Using the "button" the patient can insert a needle or catheter and deliver fluid, known as instillation, into the large intestine as an alternative to performing a rectal enema. The procedure permits use of the appendix or neoappendix to be used as a way to administer an antegrade colonic enema or an antegrade continent enema without a rectal maneuver.

Another similar procedure known as a Monti plasty procedure surgically fashions a conduit between the large intestine and an insertion stoma in the skin also for purposes of instillation of an antegrade colonic enema.

Regardless of the technique elected to create a stoma entry into the large intestine, the instillation of fluids requires an external mechanism to introduce the fluids into the stoma and therefore into the intestine. Fluid is typically introduced to sweep the large intestine of fecal matter at least once a day.

Prior to the present invention, patients who have undergone a Malone, Monti or similar procedure are required to introduce fluids into the large intestine by means of a drip consisting typically of a saline filled bag elevated above the patient with a drain tube attached at one end to the bag and terminated by a needle or catheter at the other end which is inserted into the button or piercing at the navel. Fluid is permitted to drip into the large intestine which migrates to the rectum and the flushing is accomplished. The drip procedure requires the patient to remain immobile and sitting on a commode as the fluid passes through for a period of several hours. The procedure typically requires one standard drip bag to be used.

More recently, flushing of the intestine through the entry stoma piercing has been accomplished by introducing fluids into the large intestine using a number of fluid-filled syringes. A syringe filled with the flushing fluid is attached to a needle or catheter and inserted into the piercing or button. The syringe is dispensed and then refilled periodically until the required amount of fluid is delivered. The syringe technique requires two competent people. One caretaker is required to fill the syringe. At the same time the client is responsible for pinching the catheter shut when the syringe is removed from the catheter as introduction of flushing fluid into the intestine produces back pressure. The catheter must be pinched shut to prevent fecal matter and intestinal fluid from flowing back through the catheter and out the now open catheter end. The procedure using the syringe technique requires the syringe to be refilled 10-20 times. If the client is not competent or able enough to assist, a second caretaker is needed. Many individuals requiring this type of treatment often have other handicaps that prevent them from assisting themselves. The use of multiple syringes also increases the risk of introducing air into the instillation fluid. The introduction of air into the stoma necessarily induces significant discomfort or pain in the client.

Generally, the current methods of flushing the ACE require the assistance of caretakers and require up to one hour to perform. Particularly for children, the procedure can not be performed on their own. The present invention permits self-application of an antegrade colonic enema without assistance of caretakers. Further the present invention significantly decreases the time required to perform a flush. Additionally, self-administration and short application times improve the patient's quality of life.

SUMMARY OF THE INVENTION

Accordingly, the present invention is directed to injection apparatuses and methods for injecting fluids into the human body and, more specifically, for instillation of fluids into patients who have had surgical procedures to construct a stoma entry point into the body, particularly the large intestine for purposes of administering antegrade colonic enemas, that substantially obviates one or more of the problems due to the limitations and disadvantages of the related art. As used in this specification, a client is a patient who uses the present invention.

The present invention is an automated antegrade colonic enema instillation apparatus and the method of use thereof generally comprising a fluid reservoir for containment of flushing fluid, a fluid pumping means, a pump control means for controlling a fluid pressure and flow rate, and an insertion and delivery appliance having a fluid delivery line and an intestinal stoma catheter or needle for insertion into the patient's stoma. The apparatus is optionally powered by batteries or other portable power source to provide mobility of the apparatus, improved electrical safety and to permit use of the apparatus in situations where electrical power is not available. Although the invention is intended for use for administering antegrade colonic enemas, the invention may also be used for administration of any fluid requiring a similar delivery technique.

The client fills a fluid reservoir with instillation flushing fluid. The flushing fluid is passed through the pumping device to eliminate air or gas from the pumping line by turning the apparatus on briefly to purge the lines. A pump assembly is controlled by a pump control module to drive the pump at a flow rate and pressure suitable for instillation. The pump assembly must minimize the introduction of air or gas into the flushing fluid as this can cause discomfort and pain to the client. The pump assembly is capable of delivering from 10 ml/min to 1000 ml/min. The discharge side of the pump assembly is attached to a flexible delivery line typically constructed of tubing with an internal diameter typically no more than 20 mm. The fluid delivery line should be as small as practical but preferably no smaller than 2 mm, as smaller connectors are difficult to manage and are less reliable. An intestinal stoma catheter or needle is attached to the end of the flexible delivery line for insertion into the client's intestinal stoma. The apparatus is then activated and fluid delivery begins. Experiments show that sufficient instillation fluid can be injected into the colon to administer an antegrade colonic enema procedure within 5 to 15 minutes which is significantly shorter than the administering times of all prior art.

Attention to the type of pump assembly used is important. The pump assembly should be efficient to enable the use of a portable power source. The pump assembly should be clean in that minimal foreign material is introduced into the instillation fluid. Further, the pump assembly should have minimal capacity to pump air or gas so as to minimize the introduction of air or gas into the instillation fluid. And further, the pump should not be capable of over pressuring the output lines. Additionally, the pump should be highly reliable. Gear pumps are generally reliable and permit designs which incorporate magnetically coupled drives. Intrusion of contaminants into the instillation fluid are also reduce by utilizing, magnetically coupled drives. Also the magnetically coupled drives further insulate the patient from the potential of electrical shock. Additionally the pump assembly should be capable of delivering fluid pressures in the range of 2 mm H2O to 500 mm H2O and fluid flow rates in the range of 50 ml/minute to 600 ml/minute. These volumes, pressures and flow rates, as measured at the traditional and customary one standard atmosphere and standard temperature of 0 degrees Celsius, have been shown through experimentation to produce satisfactory results.

One of the principle objectives of this present invention is to provide a measure of dignity to the client by minimizing the obviousness to others that the client is administering an antegrade colonic enema. The present invention meets this objective through a variety of improvements over the prior art including smaller size, weight, greater portability, containment of spillages, improved privacy, reduced noise, improved cleanliness and an ability for self-administration. The present invention therefore is of a size and weight so as to carry it on their person.

An objective of the present invention is to provide a method and apparatus for self-administration of antegrade colonic enemas without the need of caretakers as typically required by the prior art. Even if initial assistance to position or start the apparatus is required, the present invention manages the delivery of instillation fluid and automatically shuts off when the instillation is complete so supervision of a caretaker over the procedure is not necessary. By integrating a fluid reservoir capable of containing adequate fluid for the entire instillation procedure, an automated pumping system which is simple to start and a flexible tube delivery system allowing simple insertion into the client's stoma, the present invention meets this objective. Additionally, the invention offers greater dignity to the user by reducing or eliminating the need for caretaker involvement.

Another objective of the present invention is to provide a method and apparatus to administer the installation of fluids in a manner such that the flushing effect in the large intestine is more complete than that accomplished by the prior art. As experiments have shown, a benefit of a controlled and consistent delivery of fluid as provided by the present invention is that there tend to be fewer bowel related accidental discharges later in the day. The continuous flow also reduces the risk of the introduction of gas or air into the instillation fluid.

The method and apparatus provides a means to administer the instillation of fluids in a safe and timely and effective manner by means of a pumping control module that can provide a variety of pressure, flow rate and pumping duration control schemes whereby a specific delivery profile may be utilized to increase the effectiveness of the instillation and resulting flush while also reducing the total time of the flushing procedure.

A further objective of the present invention is to reduce the size, weight and improve the convenience of use as compared to the prior art as accomplished by the size and weight of the components of the invention. Also the invention generally improves the self-esteem and quality of life for a patient requiring antegrade colonic enemas over the prior art. The reduced size provides a means to conceal the apparatus.

The output pressure into the bowel, using the present invention, is an order of magnitude lower than the syringe method. This is particularly beneficial post-op to the stoma surgery.

A further objective of the invention is to improve the cleanliness of the enema procedure. In the present invention most components are autoclavable or dishwasher safe and those that are not are disposable. There are also fewer components in the present invention than in most prior art techniques thereby reducing the risk of point of entry contamination and retention of contaminants within the apparatus. Additionally, the reduced administering time reduces the exposure of the client to contamination.

BRIEF DESCRIPTION OF THE DRAWING

The accompanying drawings, which are incorporated in and constitute a part of this specification illustrate embodiments of the invention and, together with the description, serve to explain the features, advantages, and principles of the invention.

DESCRIPTION OF THE PREFERRED EMBODIMENT

Reference will now be made in detail to the present preferred embodiments of the invention, examples of which are illustrated in the accompanying drawings. The exemplary embodiments of this invention are shown in some detail, although it will be apparent to those skilled in the relevant art that some features which are not relevant to the invention may not be shown for the sake of clarity.

Figure 1:
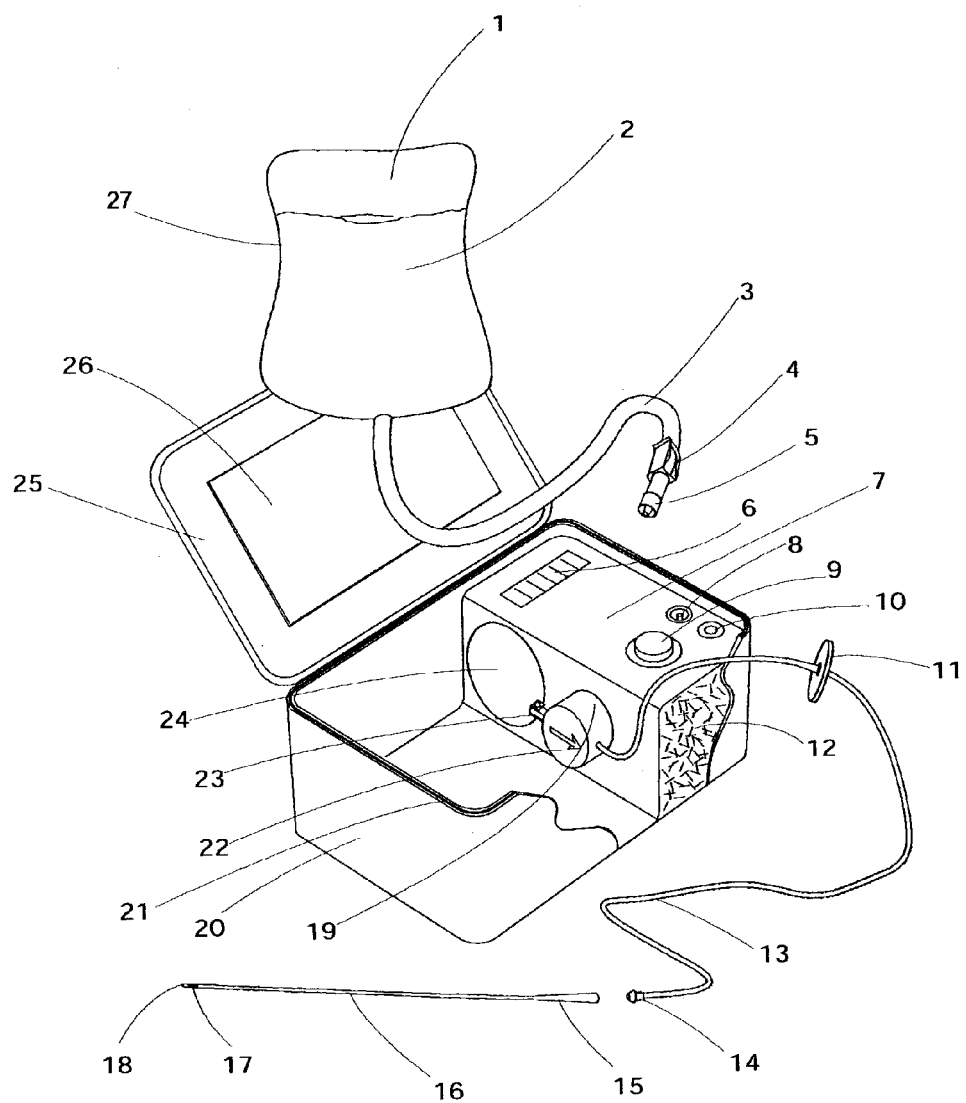
FIG. 1 is a view of a preferred embodiment of the automated instillation apparatus.

An exemplary apparatus and preferred embodiment of the present invention is represented generally in FIG. 1. The exemplary embodiment of the present invention has been represented in varying scale in order to provide clarity to the description of the invention and should not be construed as to place limits on the dimensions or characteristics thereof.

Referring to FIG. 1, the fluid reservoir 27 includes a sealable collapsible container such as a standard saline drip bag which are readily available from surgical supply dealer and pharmacists. The fluid reservoir is typically capable of containing 500 ml to 1000 ml of fluid 2, however smaller or larger bags may be utilized and in the range of 100 ml to 2000 ml. A drip bag is used to reduce or eliminate the introduction of air because the flexibility of the bag permits the bag to collapse or maintain a vacuum void 1 above the fluid. Further the fluid reservoir is detachably connected for refill or replacement by means of a locking mechanism 5 located at the end of the optional reservoir delivery tube 3. Without the reservoir delivery tube, the reservoir is attached directly to the pump assembly inlet. The delivery tube should be of a sufficient diameter to permit easy refill of the reservoir and restriction free delivery of fluid to the instillation apparatus. Additionally an optional pinch valve 4 is used to prevent fluid leakage from the fluid reservoir prior to connection to the pump assembly. The pinch valve permits the client to fill and seal the reservoir in preparation for storage and transport. In this embodiment, the reservoir is detachable, however, the reservoir need not be detachable or replaceable. The locking mechanism 5 detachably connects to the pump assembly inlet connector 23.

Further referring to FIG. 1, a number of convenience features are also included in this embodiment to improve the utility of the invention including a battery condition indicator 6 for embodiments including a battery powered supply as the portable power source, an optional mirror 26 for vanity purposes, and foam potting 12 for robustness and shock protection of the overall assembly as well as sound abatement. The case 20 includes a cover seal 21, which provides sealing between the case top 25 and the case when closed. This feature minimizes the leakage of fluid from the instillation apparatus when a leaking fluid reservoir bag is stored inside the case thereby adding convenience to the invention.

Figure 2:
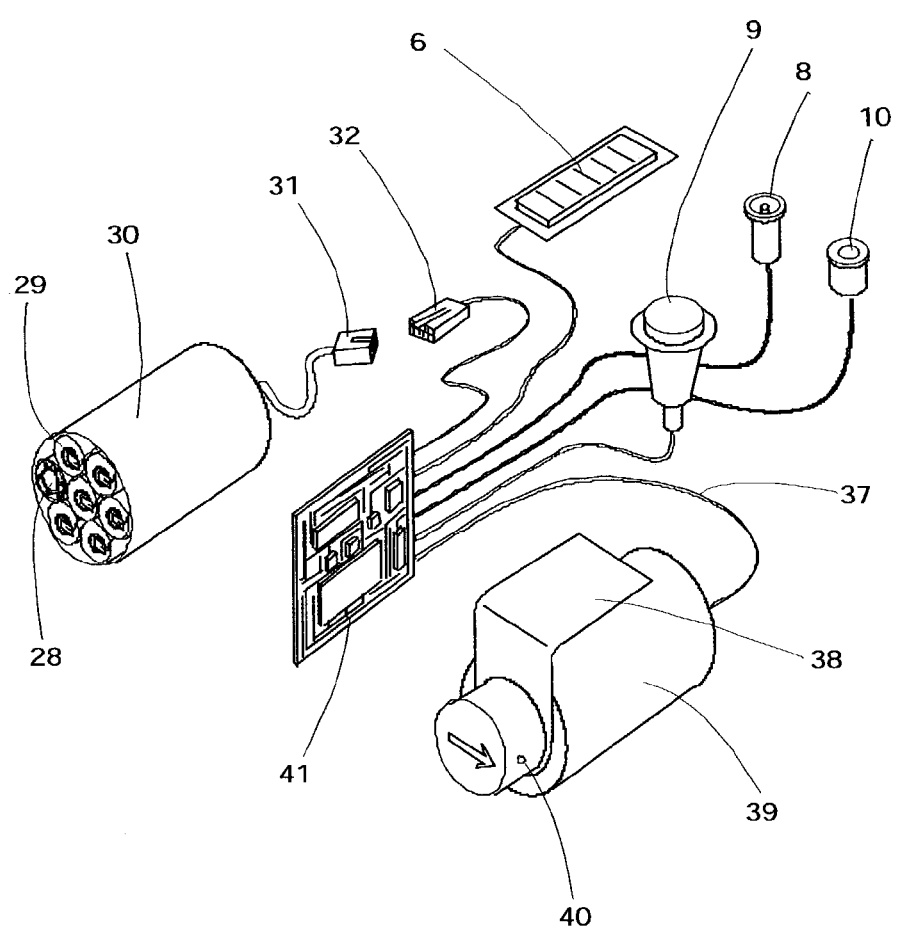
FIG. 2 is a representation of the internal components of the automated instillation apparatus.

Additionally referring to FIG. 1 and FIG. 2, fluid flows through a flexible fluid delivery line 13 attached to the pump assembly outlet 40, then through a reverse flow protection means such as a positive pressure release valve or a check valve 11. The check valve limits fluid flow to a direction from the pump assembly inlet to the pump assembly outlet thereby preventing back-flow. Optionally a pressure release valve is utilized to prevent fluid flow in the direction from the pump assembly inlet to the pump assembly outlet at low fluid pressures thus preventing leakage when the pump assembly is not active. In the case of a check valve a diaphragm check valve is preferred because of its inherent low activation pressure and the valve is also autoclavable and dishwasher safe for cleaning purposes. The check valve prevents fluid from flowing backward into the pump. During instillation of the colon, back pressure can develop. The optional positive pressure release valve thus not only prevents fluid from the colon flowing back into the pump assembly and fluid reservoir, but also prevents dribbling leakage from the intestinal stoma catheter when it is retracted from the client's stoma. The out going delivery end of the line 13 optionally may have attached a connecting device such as a barbed connector 14 or other fixing device to permit easy and secure attachment to standard catheter attachment connectors 15. Located in the end 18 of the catheter 16 are typically located holes 17 through which the flushing fluid is forced by the installation apparatus.

Also referring to FIG. 1, the battery access cover 24 permits the client to replace the custom rechargeable battery pack. The battery access cover permits access through the mounting chassis 7. The chassis also provides a convenient surface to mount the start/stop switch 9, the external auxiliary battery connector 10 and the battery charging connector 8, and battery condition indicator. In the embodiment the mounting chassis is optionally made of a continuous plate so shaped and constructed such that it is geometrically constrained within the case making the apparatus more robust and further limiting leakage or spillage fluid escaping by minimizing the number of fastener penetrations into the case.

Referring to FIG. 2, the typical operational components of the automated instillation apparatus and their connectivity are illustrated for clarity. A pumping means, in this embodiment being a pump assembly as depicted in FIG. 1 and FIG. 2 typically comprising a pump motor 39, a magnetic couple drive 19, a gear pump head 22, a pump mounting bracket 38, an inlet 23 and an outlet 40. The pump motor is an electric pump motor and is supplied power over the pump supply harness 37 from the pump control module 41. The pump control module, in this embodiment, is comprised of a means to control the pump assembly and provide connectivity of a variety of user controls and displays such as a start/stop switch 9 and a battery condition meter 6. Additionally, an external battery is optionally connected to the external auxiliary battery connection 10 permitting a client to operate the instillation apparatus by means of commonly available batteries. A battery charger connection 8 is used for attachment of a battery charger to charge the internal custom rechargeable battery pack 30. In this embodiment, a recharging means for recharging the rechargeable batteries is provided by the pump control module. The pump control module performs a number of functions including the regulation of the recharging of the custom rechargeable battery pack. Additionally, for added safety, the module prevents the instillation apparatus from operating while charging. The module also regulates the voltage and power, and the duration thereof, supplied to the pump motor. The module starts supplying the pump motor when the start/stop button is depressed and continues to supply the pump motor until a predetermined time period has expired or the start/stop button is depressed again or a predetermined volume of flushing fluid has been delivered. The pump control module determines when the predetermined volume of flushing fluid has been delivered by monitoring the pump motor current draw and stopping the pump motor when the pump motor current draw increases as the sealed collapsible fluid reservoir is depleted of fluid resulting in a vacuum on the pump assembly inlet. Optionally a fluid level sensor may be associated with a fluid reservoir that is not collapsible and sealable wherein the pump control module monitors for the fluid level in the fluid reservoir corresponding to the predetermined volume of flushing fluid required and when attained stops the pump assembly.

Further referring to FIG. 2, the custom rechargeable battery pack 30 is comprised of a plurality of rechargeable Nickel Metal Hydride battery cells 29. A battery spacer 28 is optionally included to substitute for batteries which are not required for a particular required voltage configuration. As such, the custom rechargeable battery pack output voltage and capacity can be adjusted as required for various applications of the automated instillation apparatus. The custom rechargeable battery pack is detachably connected to the pump control module by means of wiring harnesses 31 and 32. The custom rechargeable battery pack is configured with a plurality of cells typically from five to seven. The number of cells installed in the custom rechargeable battery pack is used as a means to limit the pressure and flow rates of the apparatus. During periods immediately after a Malone procedure, there is usually a requirement to deliver the instillation fluid at a lower flow rate or pressure, therefore various capacity custom rechargeable battery packs can be used to implement the required limitation.

Figure 3:
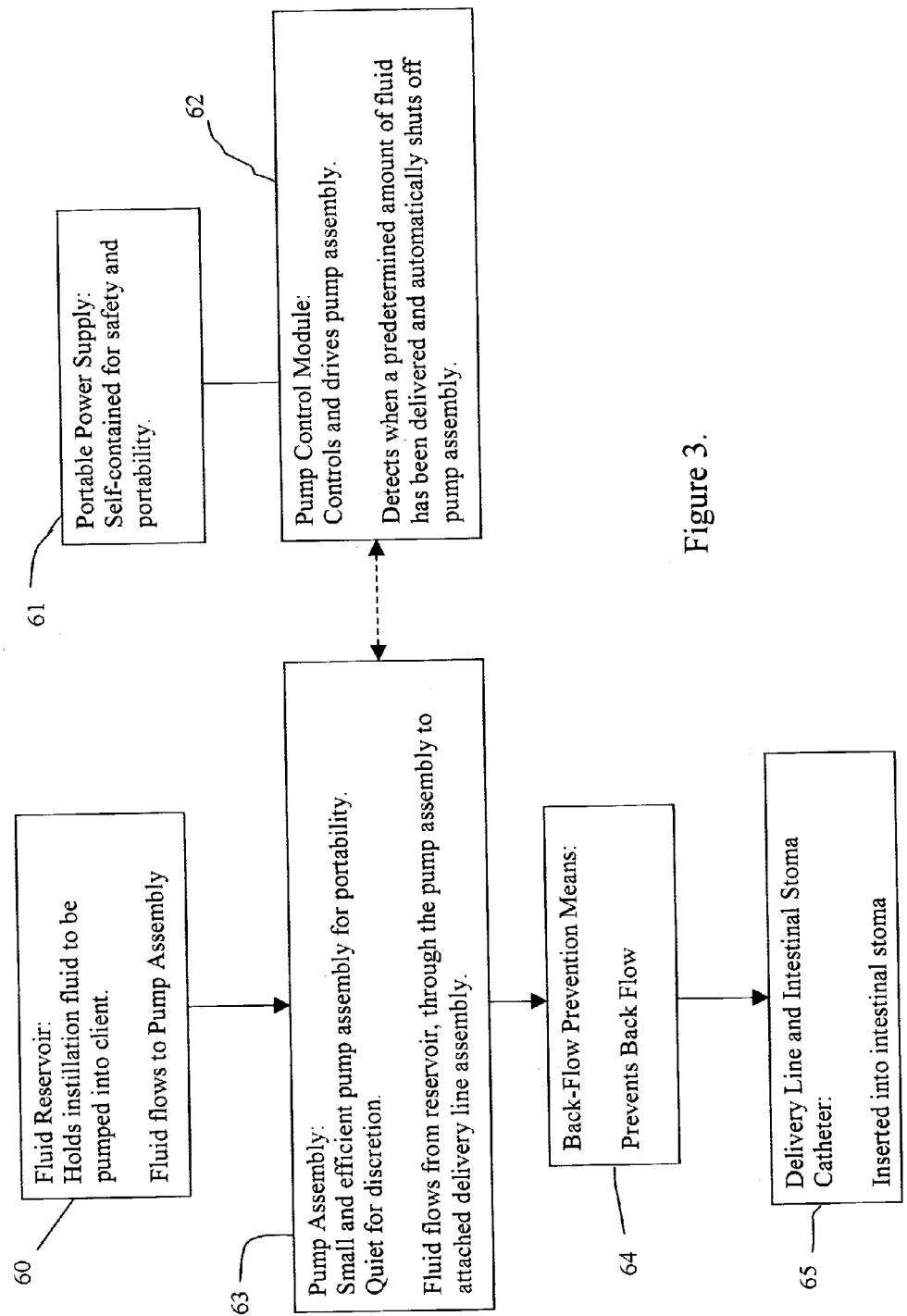
FIG. 3 is a schematic representation of the functional components of the automated instillation apparatus.

Referring to FIG. 3, the essential functional components of the invention are depicted. The fluid reservoir 60 supplies fluid to the pump assembly 63 which pumps the fluid through a check valve assembly 64 and out to the client with a stoma 65. The pump assembly is controlled by the pump control module 61 and supplied with power from the power supply 62.

Figure 4:
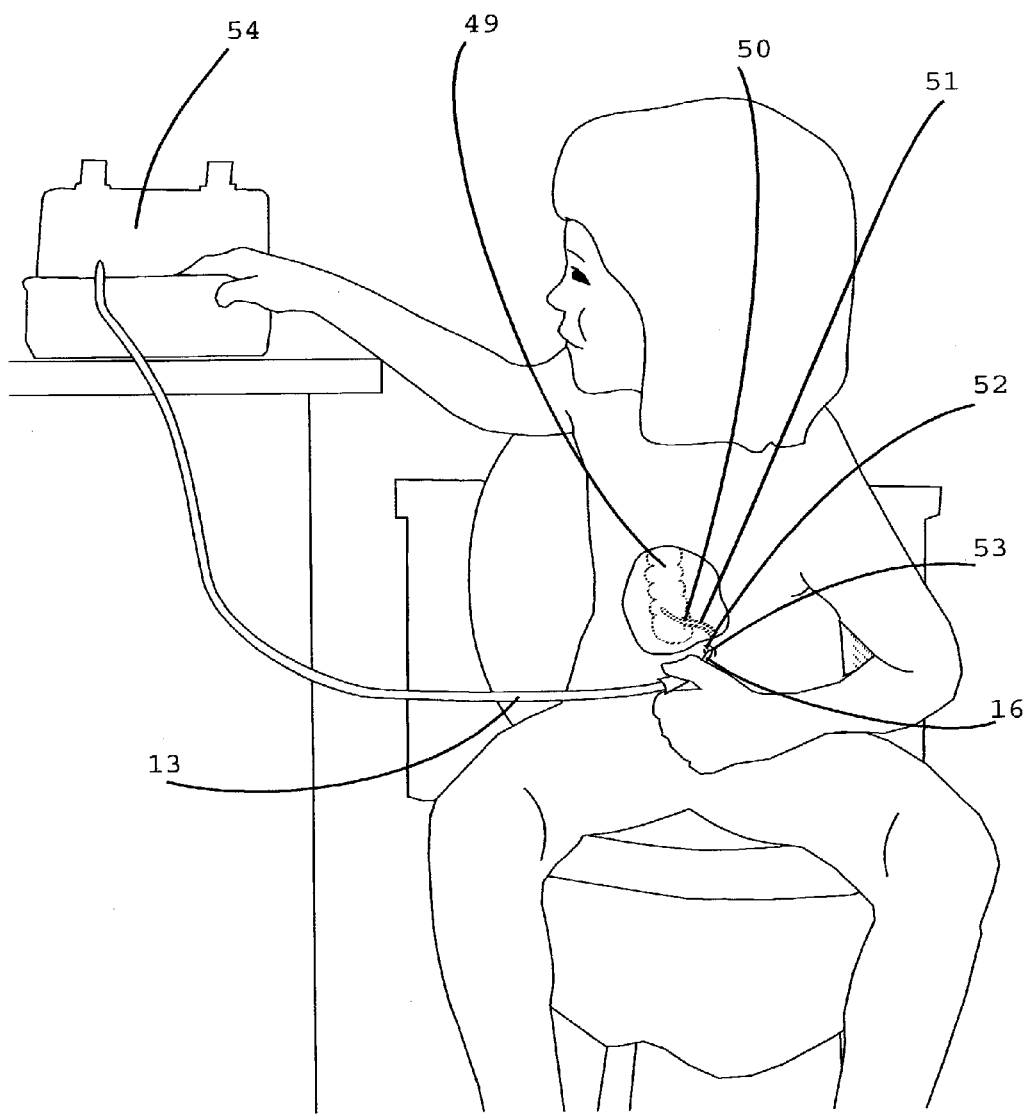
FIG. 4 is a depiction of a typical method of use of the automated instillation apparatus.

Referring to FIG. 4 which depicts a client with the automated instillation apparatus pump assembly 54 with the flexible delivery tube 13 in position, the method for application of an antegrade colonic enema using the automated instillation apparatus comprising the steps of filling the fluid reservoir with instillation fluid, inserting the intestinal stoma catheter 16 attached to the delivery tube or apparatus into the client's intestinal stoma, starting the automated instillation apparatus wherein the apparatus initiates a transfer of fluid from the reservoir producing a continuous and steady flow of installation fluid free of air or gas bubbles into the client's intestinal stoma 53 located in or near the navel 52, waiting for the automated instillation apparatus to stop and removing the delivery tube or apparatus from the client's stoma. In the Malone procedure the appendix 51, which is present on the upper colon 49, is surgically attached to the navel 52 and a flap 50 is surgically fashioned to act as a one-way valve to prevent bowel contents from leaking out.

Another embodiment of the present invention utilizes plastic water bottles commonly used for containing purified drinking water as the fluid reservoir. These bottles generally are capable of collapsing in a similar fashion to a bag reservoir.

Another embodiment of the present invention utilizes a windup pump thereby eliminating a power supply requirement.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. An automated instillation apparatus for instilling fluid into a client having an intestinal stoma thereby administering an antegrade colonic enema comprising;

a fluid reservoir being a sealable and collapsible container, a pump assembly having an inlet and an outlet, said pump assembly inlet in direct fluid communication with said fluid reservoir, said pump assembly produces a fluid flow when activated, having a gear type pump and an electric pump motor, a reverse flow prevention means for limiting said fluid flow to a direction from said pump assembly inlet to said pump assembly outlet, said reverse flow prevention means in fluid communication with said pump assembly, the reverse flow prevention means being a pressure release valve in fluid communication with said pump assembly only when a fluid pressure at said pressure release valve inlet is greater than a fluid pressure at said pressure release valve outlet by a predetermined amount of fluid pressure for preventing reverse leakage of fluid when said pump assembly is not activated, a fluid delivery line having an inlet and an outlet, said fluid delivery line inlet in direct fluid communication with said pump assembly, an intestinal stoma catheter detachably connected to said fluid delivery line outlet wherein said intestinal stoma catheter is inserted into stoma opening to the large intestine of a client to be injected with fluid for purposes of administering an antegrade colonic enema, a pump control module communicatively connected to said pump assembly, said pump control module operable to signal said pump assembly to transfer a predetermined volume of fluid by providing said pump assembly with power while measuring a current consumption of said pump motor, until said current consumption increases to a predetermined amount resulting from said electric pump motor current increase when said fluid reservoir is empty and collapsed thereby creating an increased load on the pump, whereby an automatic shutoff is effected, and a portable power source electrically connected to said pump control module.

2. An apparatus as set forth in claim 1, wherein said fluid reservoir further comprising a fluid level sensor operably associated therewith, said pump control module communicatively connected to said fluid level sensor, said pump control module operable to measure a fluid level value provided by said fluid level sensor, said pump control module to activate said pump assembly to transfer fluid until said fluid level value becomes less than a predetermined amount.

3. An apparatus as set forth in claim 1, wherein said portable power source is a plurality of battery cells each having a predetermined capacity wherein a selectable number of cells determine the maximum amount of power delivered to said pump for preventing a client from adjusting the power of the apparatus and harming themselves.

4. An apparatus as set forth in claim 1, further comprising an external battery, said external battery is detachably connected to said pump control module.

5. An apparatus as set forth in claim 1, further comprising a battery recharging means for recharging said rechargeable battery operable when said pump assembly is not signaled to transfer fluid thereby reducing the risk of electrical shock during recharging.

6. An apparatus as set forth in claim 1, wherein said fluid flow has a flow rate in the range of 50 ml/minute to 600 ml/minute.

7. An apparatus as set forth in claim 1, wherein said fluid flow has a fluid pressure in the range of 2 mm H2O to 500 mm H2O, as measured at standard temperature and pressure.

8. An apparatus as set forth in claim 1, wherein said predetermined volume of fluid is in the range of 100 ml to 2000 ml.

9. An apparatus of claim 1 being of a size and weight such that a person can easily carry said apparatus on their person.

10. A method for administering an antegrade colonic enema to a client with an intestinal stoma by means of a portable automated instillation apparatus comprising the steps of;
   providing a reservoir of a fluid to be injected into an intestinal stoma of a client, said reservoir in direct fluid communication with a portable automated instillation apparatus,
   inserting an intestinal stoma catheter in the intestinal stoma of a client,
   transferring said fluid from said reservoir into the intestinal stoma of a client by a portable automated instillation apparatus having a pumping means, said pumping means permitting no reverse flow and communicatively driven by a pump control means operable to stop fluid transfer when a predetermined amount of fluid has been transferred.

11. An automated instillation apparatus for instilling fluid into a client having an intestinal stoma thereby administering an antegrade colonic enema comprising;
   a fluid reservoir being a sealable and collapsible container,
   a pump assembly having an inlet and an outlet, said pump assembly inlet in direct fluid communication with said fluid reservoir, said pump assembly produces a fluid flow when activated, having a gear type pump and an electric pump motor,
   a reverse flow prevention means for limiting said fluid flow to a direction from said pump assembly inlet to said pump assembly outlet, said reverse flow prevention means in fluid communication with said pump assembly,
   a fluid delivery line having an inlet and an outlet, said fluid delivery line inlet in direct fluid communication with said pump assembly,
   an intestinal stoma catheter detachably connected to said fluid delivery line outlet wherein said intestinal stoma catheter is inserted into stoma opening to the large intestine of a client to be injected with fluid for purposes of administering an antegrade colonic enema,
   a pump control module communicatively connected to said pump assembly, said pump control module operable to signal said pump assembly to transfer a predetermined volume of fluid, and
   a portable power source electrically connected to said pump control module.

* * * * *